United States Patent [19]
Yamamoto et al.

[11] Patent Number: 5,754,288
[45] Date of Patent: May 19, 1998

[54] OPTICAL MEASURING METHOD OF EXPIRATION COMPONENTS

[75] Inventors: Hiroshi Yamamoto; Harumi Uenoyama; Xiaoming Dou; Yung Xiang Wang; Kentaro Shimada, all of Kyoto, Japan

[73] Assignee: Kyoto Dai-Ichi Kagaku Co., Ltd., Kyoto, Japan

[21] Appl. No.: 694,342

[22] Filed: Aug. 8, 1996

[30] Foreign Application Priority Data

Aug. 9, 1995 [JP] Japan ..................... 7-225899

[51] Int. Cl.⁶ .................. G01J 3/44; G01I 21/65
[52] U.S. Cl. .................................... 356/301
[58] Field of Search ........................... 356/301

[56] References Cited

U.S. PATENT DOCUMENTS

| | | | |
|---|---|---|---|
| 4,648,714 | 3/1987 | Benner et al. | 356/301 |
| 4,784,486 | 11/1988 | Van Wagenen et al. | 356/301 |
| 5,046,846 | 9/1991 | Ray et al. | 356/325 |
| 5,317,378 | 5/1994 | Mould et al. | 356/301 |
| 5,450,193 | 9/1995 | Carlsen et al. | 356/301 |
| 5,481,113 | 1/1996 | Dou et al. | 356/301 |

FOREIGN PATENT DOCUMENTS 61-83922  4/1986  Japan ..................... 356/326

*Primary Examiner*—F. L. Evans
*Attorney, Agent, or Firm*—Nikaido, Marmelstein, Murray & Oram LLP

[57] ABSTRACT

As to respective expiration components to be measured, wavelengths having excellent correlations between component concentrations and Raman spectral intensity values are previously selected as measuring wavelengths which are specific to the components, an expiration specimen is irradiated with Raman excitation light, Raman spectra at the measuring wavelength which is specific to nitrogen and those at the measuring wavelengths previously selected for the components to be measured respectively are measured, Raman spectral intensity ratios of the components to the Raman spectral intensity of nitrogen are obtained, and the respective expiration components are quantitatively analyzed through a calibration curve which is previously prepared as to the Raman spectral intensity ratios of the respective components to nitrogen and concentrations. It is possible to provide a measuring method utilizing Raman spectroscopy, which can directly determine intra-expiratory components in a short time with no requirement for expendable items.

8 Claims, 12 Drawing Sheets

SAMPLE

OPTICAL MEASURING METHOD OF EXPIRATION COMPONENTS

BACKGROUND OF THE INVENTION

1. Field of the Invention

The present invention relates to a method of measuring the concentrations (or abundances or abundance ratios) of expiration components such as acetone, acetaldehyde, isoprene, ammonia, butyric acid, valeric acid, oxygen, nitrogen, carbon dioxide and the like, for example, with a relatively low-priced apparatus in a short time.

2. Description of the Background Art

Expiration contains at least 400 types of volatile compounds. It is now being clarified that these expiration components are closely related to various diseases such as diabetes mellitus, hepatopathy, nephropathy, congenital amino acid metabolism abnormality, enteric fermentation, malabsorptions of carbohydrate, hyperoxidation of intravital lipid and the like, intoxication by chemical substances and the like. Further, these are extremely important substances in clinical diagnostics due to specific odors. The merit of an expiration test resides in noninvasiveness with easiness in specimen collection as compared with blood or the like. Thus, the expiration test can reduce physical and mental loads of the subject in specimen collection.

Methods of analyzing test gas components include gas chromatography, gas chromatography/mass spectrometry (GC/MS), tandem mass spectrometry, an IR method (infrared spectral method), a semiconductor sensor method and the like.

The gas chromatography or gas chromatography/mass spectrometry is adapted to separate and purify an expiratory specimen which is inspissated with some means by a gas chromatograph or a gas chromatograph/mass spectrometer for thereafter determining the same. A flame ionization detector (FID) is mainly employed as a detector for the gas chromatograph. Alternatively, a flame photometric detector (FPD) or a photoionization detector (PID) may be employed.

While the flame ionization detector can determine a number of compounds, this detector has low sensitivity for inorganic compounds and sulfides. On the other hand, the flame photometric detector and the photoionization detector are higher in sensitivity than the flame ionization detector for sulfides and for halogenated hydrocarbon and unsaturated compounds respectively.

In general, the gas chromatography and the gas chromatography/mass spectrometry have such disadvantages that calibration and maintenance are frequently required in employment of apparatuses and it is difficult to use these methods as general purpose methods since the sensitivity for each substance varies with the detector. Further, highpriced apparatuses are required and the operations are troublesome.

The tandem mass spectrometry is a recently developed analyzing technique, which can separate compounds on the basis of mass-to-charge ratios. Therefore, this method requires no separation by gas chromatography or the like and has high sensitivity, while an apparatus is at an extremely high cost.

The IR method is capable of identification of a number of components and determination in high sensitivity. However, the spectra of samples containing substances having similar molecular structures such as hydrocarbon and compounds having the same substituents are considerably similar to each other and hard to identify.

A sensor which is employed in the semiconductor sensor method is fabricated by employing an oxide such as titanium oxide or copper oxide as a semiconductor material, converting the same to a nonstoichiometric composition oxide by a heat treatment and providing semiconductor characteristics thereto. This sensor utilizes the fact that the band structure in a semiconductor is changed when test gas is adsorbed by the semiconductor to change its electric resistance and electric capacitance, for detecting the test gas from the change of the electric characteristics. However, the semiconductor sensor is also sensitive to oxygen partial pressure in principle and its electric resistance and electric capacitance are changed not only by the test gas but the oxygen partial pressure. Therefore, the semiconductor sensor is problematic in reliability under such environment that oxygen is present and its partial pressure is changed.

There is also a method utilizing Raman spectroscopy. Each of Japanese Patent Laying-Open Gazettes Nos. 6-229914 (1994) and 6-229915 (1994) discloses a gas detector which introduces an output of a high output optical pulse generator into a Raman fiber member for detecting presence/absence of gas from change of the optical output, and Japanese Patent Laying-Open Gazette No. 6-242002 (1994) discloses a method of measuring the composition and concentration of a mixed gas in a respiratory tract. The former merely confirms presence/absence of the gas with no concentration measurement and identification of various components, while the latter is an anesthetic monitor for controlling/adjusting anesthesia in an operation. The Raman spectroscopy has not yet been utilized as a clinical test method of detecting various expiration components or measuring concentrations.

When a specimen is prepared from expiration, the measured expiration volume must be strictly controlled and kept constant, in order to make quantitative measurement. However, the amount of expiration exhaled by a human in a single breath depends on a personal equation, and it is not easy to collect a constant amount since the object is gas.

SUMMARY OF THE INVENTION

An object of the present invention is to provide a method of simply measuring concentrations (abundances or abundance ratios) of expiration components such as acetone, acetaldehyde, isoprene, ammonia, butyric acid, valeric acid, oxygen, nitrogen, carbon dioxide and the like, for example, at a relatively low cost in a short time.

In order to solve the aforementioned problems, the present invention utilizes the fact that the intra-expiratory components have specific Raman spectra respectively and hence it is possible to distinguish the respective components from each other in mixed gas and to measure the concentrations thereof.

In a method according to a first aspect of the present invention, respective components are quantitatively measured on the basis of a nitrogen concentration in expiration, in order to correct fluctuation of an expiration collection amount. When nitrogen which occupies about 78 percent by volume of air is inhaled in the lungs through a breath or the like is not metabolized but discharged. Therefore, the nitrogen concentration in the discharged expiration is substantially constant with a small personal equation. Namely, nitrogen having a stable concentration is utilized as a reference component, thereby measuring the concentrations of other expiration components while eliminating a personal equation and converting the data to absolute values.

Namely, the method according to the first aspect of the present invention is a measuring method of previously selecting wavelengths having excellent correlations between component concentrations and Raman spectral intensity values as to respective expiration components to be measured as measuring wavelengths which are specific to the components, irradiating an expiration specimen with Raman excitation light, measuring Raman spectra at the measuring wavelength which is specific to nitrogen and those at the measuring wavelengths previously selected for the components to be measured respectively, obtaining Raman spectral intensity ratios of the components to the Raman spectral intensity of nitrogen, and quantitatively analyzing the respective intra- expiratory components through a calibration curve which is previously prepared as to the Raman spectral intensity ratios of the respective components to nitrogen and the concentrations.

According to this method, it is possible to readily measure the absolute values of the respective component concentrations also as to expiration from which a constant amount of specimen cannot be readily collected.

A method according to a second aspect of the present invention utilizes the fact that respective expiration components have specific Raman spectra respectively and hence it is possible to distinguish the respective components from each other in mixed gas and to measure the concentrations thereof, and obtains concentration ratios of a plurality of components in order to correct fluctuation of an expiration collection amount.

Namely, the method according to the second aspect of the present invention is a measuring method of previously selecting wavelengths having excellent correlations between component concentrations and Raman spectral intensity values as to a plurality of expiration components to be measured as measuring wavelengths which are specific to the components, irradiating an expiration specimen with Raman excitation light, measuring Raman spectra at the measuring wavelengths which are previously selected for the plurality of components respectively, and obtaining concentration ratios of the plurality of components through calibration curves which are previously prepared as to the Raman spectral intensity values and the concentrations on the respective components.

It is possible to obtain correct concentration ratios of a plurality of components by obtaining the concentration ratios of the plurality of components also as to expiration from which a constant amount of specimen cannot be readily collected.

The measuring method according to the present invention simply irradiates an expiration specimen with Raman excitation light, whereby the expiration components can be directly determined in a short time, with no requirement for expendable items.

The wavelength having an excellent correlation between each component concentration and Raman spectral intensity is a wavelength having a correlation coefficient R of at least 0.8, preferably at least 0.9. The correlation coefficient R is a value measured as to a sample of a plurality of concentrations independently containing each component and calculated by the following equation (1):

$$R = \frac{\Sigma[(xi - X)(yi - Y)]}{\sqrt{[\Sigma (xi - X)^2][\Sigma (yi - Y)^2]}} \quad (1)$$

where xi represents the concentration of each point of each component, yi represents Raman spectral intensity with respect to xi, X represents the average concentration of each component, and Y represents the average Raman spectral intensity.

Oxygen, nitrogen, carbon dioxide, water vapor, acetone, acetaldehyde, ammonia, isoprene, isobutyric acid, n-butyric acid, isovaleric acid, n-valeric acid, propionic acid, ethanol and the like are contained as expiration components to be measured. Preferable measuring wavelengths for the respective components, which are wavelengths having correlation coefficients R in the above equation (1) of at least 0.9, can be selected:

from around 1530 to 1590 $cm^{-1}$ in wavenumber for oxygen, from around 2304 to 2364 $cm^{-1}$ in wavenumber for nitrogen, from around 1255 to 1315 $cm^{-1}$ or around 1335 to 1415 $cm^{-1}$ in wavenumber for carbon dioxide, from around 751 to 811 $cm^{-1}$, around 1706 to 1766 $cm^{-1}$, around 2680 to 2740 $cm^{-1}$, around 2830 to 2967 $cm^{-1}$ or around 2967 to 3054 $cm^{-1}$ in wavenumber for acetone, from around 488 to 518 $cm^{-1}$, around 841 to 901 $cm^{-1}$, around 895 to 955 $cm^{-1}$, around 1084 to 1144 $cm^{-1}$, around 1369 to 1468 $cm^{-1}$, around 1722 to 1782 $cm^{-1}$, around 2666 to 2786 $cm^{-1}$, around 2786 to 2890 $cm^{-1}$ or around 2906 to 2966 $cm^{-1}$ in wavenumber for acetaldehyde, from around 494 to 585 $cm^{-1}$, around 751 to 811 $cm^{-1}$, around 924 to 1042 $cm^{-1}$, around 1047 to 1107 $cm^{-1}$, around 1273 to 1343 $cm^{-1}$, around 1358 to 1463 $cm^{-1}$, around 1619 to 1679 $cm^{-1}$, around 2715 to 2775 $cm^{-1}$, around 2849 to 2909 $cm^{-1}$, around 2896 to 2975 $cm^{-1}$, around 2975 to 3059 $cm^{-1}$, around 3074 to 3144 $cm^{-1}$ or around 3466 to 3526 $cm^{-1}$ in wavenumber for isoprene, from around 3198 to 3258 $cm^{-1}$ or around 3315 to 3375 $cm^{-1}$ in wavenumber for ammonia, from around 1254 to 1314 $cm^{-1}$, around 1357 to 1417 $cm^{-1}$ or around 2871 to 3018 $cm^{-1}$ in wavenumber for isobutyric acid, from around 2866 to 2926 $cm^{-1}$, around 2951 to 3011 $cm^{-1}$ or around 3011 to 3067 $cm^{-1}$ in wavenumber for n-butyric acid, from around 2829 to 2889 $cm^{-1}$, around 2951 to 3011 $cm^{-1}$ or around 3011 to 3067 $cm^{-1}$ in wavenumber for isovaleric acid, from around 2945 to 3005 $cm^{-1}$ or around 3005 to 3061 $cm^{-1}$ in wavenumber for n-valeric acid, from around 2875 to 2935 $cm^{-1}$ or around 2935 to 2962 $cm^{-1}$ in wavenumber for propionic acid, and from around 853 to 913 $cm^{-1}$, around 2852 to 2910 $cm^{-1}$, around 2910 to 3008 $cm^{-1}$ or around 3630 to 3690 $cm^{-1}$ in wavenumber for ethanol.

Peak positions of these substances suitable for quantitative measurement are shown in FIG. 17 together. All numerical values appearing in FIG. 17 represent wavenumbers ($cm^{-1}$).

It is conceivable that the peak of oxygen around 1555 $cm^{-1}$ is by vibration from O=O.

It is conceivable that the peak of nitrogen around 2331 $cm^{-1}$ is by vibration from N≡N.

It is conceivable that the peaks of carbon dioxide around 1283 $cm^{-1}$ and around 1385 $cm^{-1}$ are by totally symmetric stretching vibration.

It is conceivable that the peaks of acetone around 805 $cm^{-1}$, around 1080 $cm^{-1}$, around 1429 $cm^{-1}$ and around 2940 $cm^{-1}$ are by vibration from $CH_3$, the peak around 1237 $cm^{-1}$ is by vibration from $CH_3C$, and the peak around 1710 $cm^{-1}$ is by vibration from CO.

It is conceivable that the peaks of acetaldehyde around 518 $cm^{-1}$ and around 1124 $cm^{-1}$ are by vibration from C—C=O, the peak around 871 $cm^{-1}$ is by vibration from $CH_3$, the peaks around 925 $cm^{-1}$, around 1438 $cm^{-1}$, around 2860 $cm^{-1}$ and around 2936 $cm^{-1}$ are by vibration from $CH_3$, the peaks around 1399 $cm^{-1}$, around 2696 $cm^{-1}$ and around 2817 $cm^{-1}$ are by vibration from CH, the peak around 1753 $cm^{-1}$ is by vibration from C=O, and the peaks around 2725 $cm^{-1}$ and around 2836 $cm^{-1}$ are by resonance from CH.

It is conceivable that the peaks of isoprene around 524 $cm^{-1}$, around 555 $cm^{-1}$ and around 1078 $cm^{-1}$ are by vibration from CCC, the peaks around 1002 $cm^{-1}$, around 1303 $cm^{-1}$ and around 3104 $cm^{-1}$ are by vibration from CH, the peaks around 781 $cm^{-1}$, around 2926 $cm^{-1}$, around 3001 $cm^{-1}$ and around 3029 $cm^{-1}$ are by vibration from $CH_2$, the peaks around 954 $cm^{-1}$, around 1388 $cm^{-1}$, around 1433 $cm^{-1}$, around 2879 $cm^{-1}$ and around 2945 $cm^{-1}$ are by vibration from $CH_3$, and the peak around 1649 $cm^{-1}$ is by vibration from CC.

It is conceivable that the peak of ammonia around 3228 $cm^{-1}$ is vibration from $NH_2$, and the peak around 3345 $cm^{-1}$ is vibration from $NH_3$.

It is conceivable that the peak of isobutyric acid around 1284 $cm^{-1}$ is vibration from COOH, the peaks around 1387 $cm^{-1}$, around 2940 $cm^{-1}$ and around 2988 $cm^{-1}$ are vibration from $CH_3$, and the peak around 2901 $cm^{-1}$ is vibration from $CH(CH_3)_2$.

It is conceivable that the peak of n-butyric acid around 2896 $cm^{-1}$ is vibration from $CH_2$, the peak around 2981 $cm^{-1}$ is vibration from $CH_3$, and the peak around 3037 $cm^{-1}$ is vibration from COOH.

It is conceivable that the peak of isovaleric acid around 2858 $cm^{-1}$ is vibration from $CHCH_3$ and $CH_3$, the peak around 2981 $cm^{-1}$ is vibration from $CH_3$, and the peak around 3037 $cm^{-1}$ is vibration from COOH.

It is conceivable that the peak of n-valeric acid around 2975 $cm^{-1}$ is vibration from $CH_3$, and the peak around 3031 $cm^{-1}$ is vibration from COOH.

It is conceivable that the peak of propionic acid around 2906 $cm^{-1}$ is vibration from $CH_2$, the peak around 2962 $cm^{-1}$ is vibration from $CH_3$, and the peak around 3037 $cm^{-1}$ is vibration from COOH.

It is conceivable that the peak of ethanol around 883 $cm^{-1}$ is vibration from CCO, the peaks around 2883 $cm^{-1}$ and around 2978 $cm^{-1}$ are vibration from $CH_3$, and the peak around 2940 $cm^{-1}$ is vibration from $CH_2$.

The present invention is used as a technique of a clinical test for a specimen of expiration. About 400 types of compounds derived from an organism are present in expiration. While carbon dioxide, acetone, ethanol, acetaldehyde, ammonia and the like are contained in the expiration in addition to nitrogen and oxygen which are principal components of the atmosphere, each component concentration of a normal person presents a personal equation, and significant difference is observed between a normal person and a patient who contracts a certain disease. Further, the concentrations of the components contained in expiration are at various levels from ppm to ppb levels. In the method according to the first aspect of the present invention, absolute concentrations of these various components can be obtained on the basis of the nitrogen concentration in the expiration.

Carbon dioxide is an index for a hyperventilation syndrome. The term "hyperventilation syndrome" indicates such a state that overventilation is caused by a severe neurosis or hysterics of a young woman, the amount of carbon dioxide excreted from arterial blood is abnormally increased, and the ratio of bicarbonic acid to carbonic acid is increased to increase pH, resulting in hyper respiratory alkalosis. If excreted expiration has a high carbon dioxide concentration, therefore, the hyperventilation syndrome can be judged.

Most parts of intra-expiratory ketone bodies such as acetone are generated as intermediate metabolites of β-oxidation reaction of lipid in the liver. In a pathologic state of diabetes mellitus or the like, fatty acids are utilized in such a large amount that the organism cannot completely use metabolites of the fatty acids but acetone from the liver is emergent in the blood and the intra-expiratory acetone concentration is increased simultaneously with increase of the intravascular concentration. After insulin treatment for diabetes mellitus, particularly IDDM (insulin dependent diabetes mellitus), utilization of blood glucose of the patient is increased and hence oxidation of fatty acids is reduced. Therefore, the concentrations of ketone bodies which are metabolites of the intravascular fatty acids are reduced, and the intra-expiratory acetone concentration is also reduced. This serves as an effective index for judgement of a curative effect for the diabetes mellitus, and can also serve as an index for self administration of the diabetic. Further, it is useful for monitoring or administration in case of starvation, overexercise or obesity.

Intra-expiratory ethanol and acetaldehyde are extremely useful in diagnosis and process observation of alcohol metabolism in case of alcoholism (drunkenness). Also in congenital acetaldehyde decomposition enzyme deficiency, measurement of the intra-expiratory acetaldehyde concentration is effective for its diagnosis.

In case of a hepatic disease, ammonia is collected in the blood due to impossibility of metabolism to urea, and the amount of ammonia discharged in the expiration is increased. In more concrete terms, intra-expiratory ammonia is significantly increased in case of hepatic insufficiency or renal insufficiency (uremia).

VFAs (volatile fatty acids) such as acetic acid, propionic acid, butyric acid and valeric acid result from food fermentation by enteral microorganisms, and the balance of the enteral microorganism group is changed in case of a hepatic disease or amino acid metabolism abnormality, such that the enterally produced VFAs are increased in amount and discharged in the expiration.

The expiration of the patient of a certain congenital disease such as phenylketonuria (genetic deficiency of phenylalanine 4-monooxygenase inverting phenylalanine which is aromatic amino acid to tyrosine) or isovalericacidemia (genetic deficiency of isovaleryl-CoA dehydrogenase in a leucine metabolic process) has a specific odor, since phenylacetic acid or isovaleric acid is discharged in the expiration.

The concentration ratios of a plurality of components obtained by the method according to the second aspect of the present invention are useful for diagnosis of measurement of a respiratory quotient or the like. The term "respiratory quotient" indicates the ratio of a carbon dioxide expired amount to an oxygen absorbed amount (carbon dioxide expired amount/oxygen absorbed amount) in breathing of an individual. The carbon dioxide expired amount can be obtained from Raman spectral intensity of carbon dioxide in expiration through a calibration curve, while the oxygen absorbed amount can be obtained by multiplying a relative value of a nitrogen concentration obtained from the Raman spectral intensity of nitrogen in the expiration through the calibration curve by the ratio of oxygen to nitrogen in the air. Thus, the respiratory quotient can be obtained by measuring Raman spectral intensity values of carbon dioxide and nitrogen in the expiration. The respiratory quotient is around 0.8 in a starvation state, and reduced in case of diabetes mellitus.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

While the present invention is now described in more concrete terms with reference to an embodiment, the present invention is not restricted to this.

Figure 1:
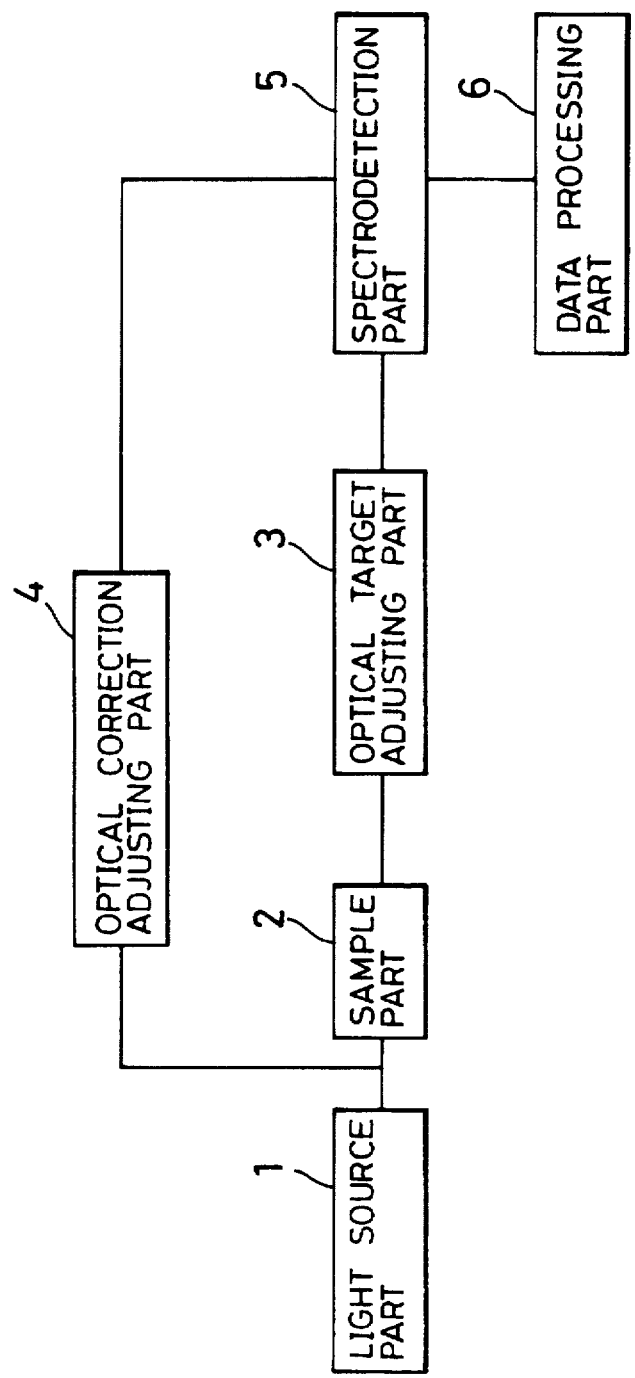
FIG. 1 is a block diagram schematically showing a measuring apparatus to which the method of the present invention is applied.
Figure 2:
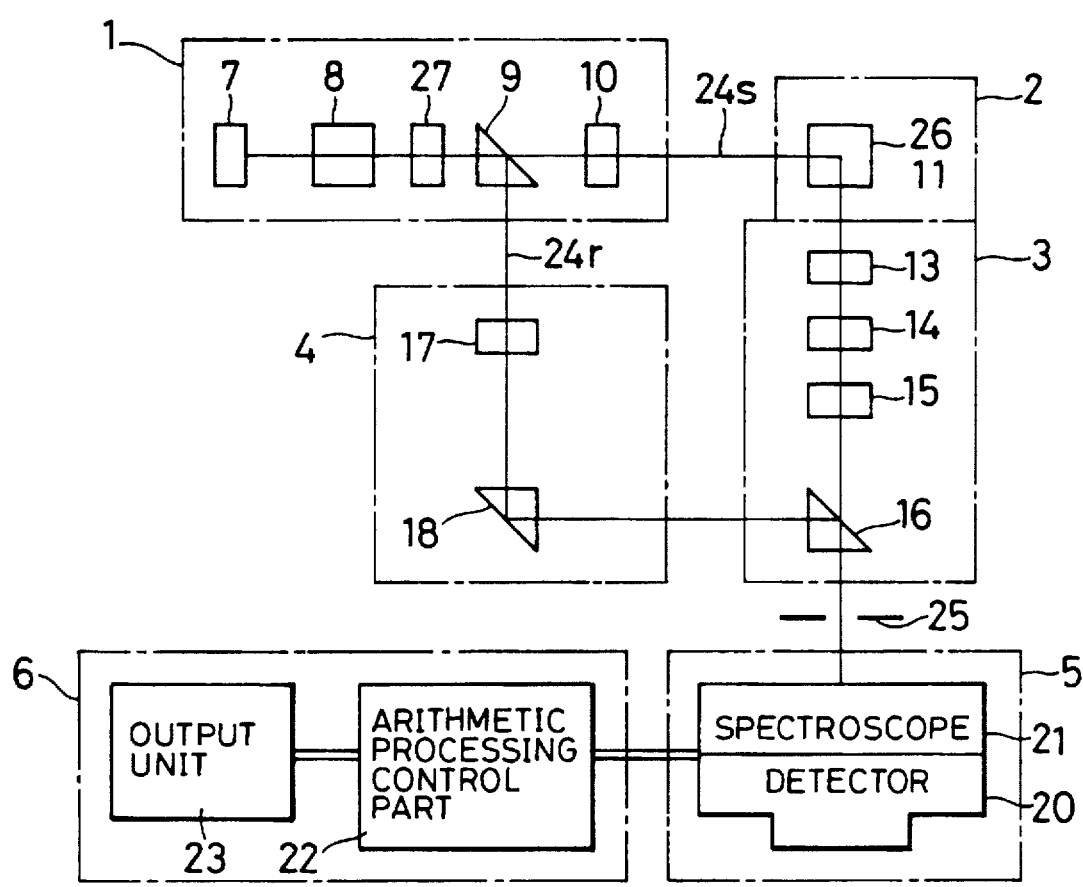
FIG. 2 is a concrete apparatus structural diagram illustrating the block diagram of FIG. 1 in detail.

An exemplary measuring apparatus for carrying out the inventive measuring method is shown in FIGS. 1 and 2.

FIG. 1 is a block diagram showing the structure of the apparatus, which consists of a light source part 1, a sample part 2, an optical target adjusting part 3, an optical correction adjusting part 4, a spectrodetection part 5 and a data processing part 6.

FIG. 2 shows a concrete example illustrating the block diagram of FIG. 1 in detail. The light source part 1 comprises an excitation light source 7, a bandpass filter 27 which transmits only excitation light from the excitation light source 7 while reflecting other light, a half mirror 9 which divides a beam from the excitation light source 7 into a sample beam 24s and a correction beam 24r, and a light source condenser lens 8 and a condenser lens 10 for converging the sample beam 24s on a sample 11 of the sample part 2.

The light source 7 is prepared from a laser unit, for example. The laser unit can be prepared from a continuously oscillating Ar ion laser unit, a Kr ion laser unit, an He-Ne laser unit, an He-Cd laser unit or an Nd:YAG laser unit, laser diodes or a pulse laser unit, and can be selected from laser units of a wide wavelength range from near ultraviolet to near infrared regions. Alternatively, a light source such as a halogen lamp generating multi-wavelength light can be utilized in combination with a spectroscope as a light source other than the laser unit.

The expiration sample 11 is stored in a cell 26 and set in the sample part 2, and irradiated with the sample beam 24s. The expiration sample 11 can be temporarily stored in a Tedlar bag (registered trade mark of E. I. du Pont de Nemours and Co.), for example, to be thereafter supplied to the cell 26. The cell 26 may be either a bottomed cell or a flow cell.

The optical target adjusting part 3 comprises filter means 14 which removes the same wavelength component as excitation light from scattered light generated from the sample 11 stored in the sample cell 26 and irradiated with the sample beam 24s, and optical systems 13 and 15 adjusting beams for converging the scattered light on an inlet slit 25 of a spectroscope. A half mirror 16 serving as wave combining means for placing the sample beam 24s from the optical target adjusting part 3 and the correction beam 24r outgoing from the optical correction adjusting part 4 on the same optical path is provided on an outlet position of the optical target adjusting part 3.

The filter means 14 in the optical target adjusting part 3 is preferably formed by a holographic notch filter including the excitation light wavelength in its notch region, or a cut filter shielding the excitation light wavelength and a shorter wavelength side therefrom.

The holographic notch filter is adapted to shield only a desired wavelength region, and transmit wavelength light of other regions. When a holographic notch filter including the excitation light wavelength in the shielded region (notch region) is employed, the sample beam 24s outgoing from the optical target adjusting part 3 includes only a target light component.

The holographic notch filter 14 is available from Kaiser Optical Systems, Inc. (U.S.A.), for example. The holographic notch filter has characteristics of completely shielding wavelength light included in the notch region and transmitting at least 80% of light of wavelength regions other than the notch region, for example.

The optical correction adjusting part 4 comprises a neutral density filter 17 for damping the light quantity of the correction beam 24r which is divided by the half mirror 9 in the excitation light source 1, and a mirror 18 for bending the optical path. The correction beam 24r is adapted to correct fluctuation of spectral light intensity caused by fluctuation of excitation light intensity from the light source 7. If such correction is not required, the half mirror 9 in the light source part 1, the optical correction adjusting part 4 and the half mirror 16 which is wave combining means are unnecessary.

The correction beam 24r, which includes only the excitation light from the light source 7 and is not passed through the sample 11, is not dependent on the sample 11 but expresses intensity fluctuation from the light source 7 with fidelity.

The spectrodetection part 5 comprises a spectroscope 21 which incorporates the sample beam 24s from the optical target adjusting part 3 and the correction beam 24r outgoing from the optical correction adjusting part 4 from the half mirror 16 through the inlet slit 25 for separating the same into spectral components thereof, and a detector 20 detecting the spectral light components separated by the spectroscope 21.

The spectrodetection part 5 is preferably a polychrometer which comprises a multi-channel photodetector for simultaneously detecting wavelength regions to be measured. When the spectrodetection part 5 is a polychrometer, it is possible to simultaneously detect the wavelength regions to be measured, and to simultaneously detect a target light spectrum of prescribed region and an excitation light. Consequently, no difference is caused between detection times of the respective wavelengths of the target light and the excitation light. If difference can be permitted between the detection times of the respective wavelengths of the target light and the excitation light, however, the spectrodetection part 5 may comprise a wavelength scanning type spectroscope and a single-channel photodetector as the spectroscope 21 and the detector 20 respectively, for successively detecting the wavelength regions to be measured.

The data processing part 6 comprises an arithmetic processing control part 22 and an output unit 23, and has a function of correcting target light intensity on the basis of detected intensity of the excitation light component in the spectrum detected by the detector 20 of the spectroscope 5.

The arithmetic processing control part 22 controls operations of the respective parts, performs spectral analysis or multivariate analysis of signals detected by the spectrodetection part 5, also performs data processing of correcting detected intensity of the target light on the basis of detected intensity of the excitation light component in the spectrum detected by the spectrodetection part 5, calculates Raman scattering spectra in which fluctuation of the light source is corrected, and also performs identification and determination of the sample 11 from the target light intensity. The output unit 23 is a printer or a display outputting data processed by the arithmetic processing control part 22.

Describing the operation of this embodiment, the sample beam 24s from the light source part 1 is applied to the sample 11 of the sample part 2. The same wavelength component as the excitation light is removed from scattered light from the sample 11 through the optical target adjusting part 3, so that the scattered light is passed through the half mirror 16 and the inlet slit 25, and incident upon the spectroscope 21. On the other hand, the light quantity of the correction beam 24r divided by the half mirror 9 in the excitation light source part 1 is adjusted through the optical correction adjusting part 4, so that the correction beam 24r is passed through the half mirror 16 and the inlet slit 25, and incident upon the spectroscope 21. The correction beam 24r corrects fluctuation of spectral light intensity caused by fluctuation of the excitation light intensity, so that Raman spectral intensity of each component is detected.

Assuming that θ represents an angle which is formed by a measuring direction for the scattered light from the expiration sample 11 to incident light, θ=90° in the measuring apparatus shown in FIG. 2, while the present invention is not restricted to this but the angle θ may be in the range of 0°≦θ<360°.

Figure 3A:
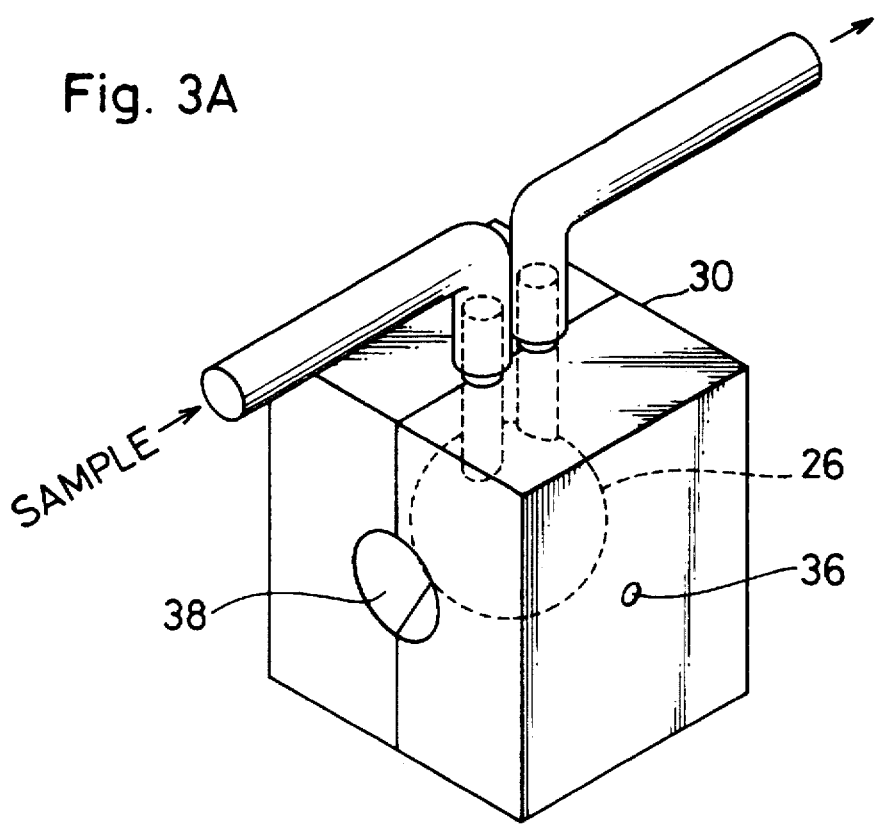
FIG. 3A is a perspective view of a spherical integration type cell holder.
Figure 3B:
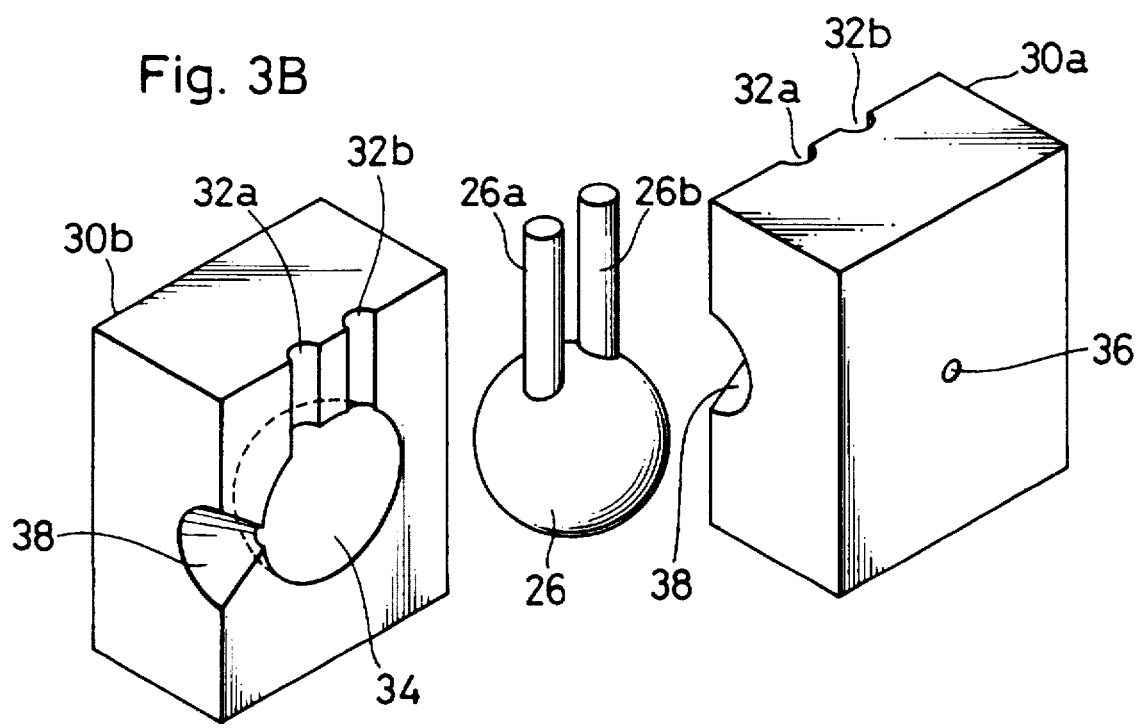
FIG. 3B is an exploded perspective view of the cell and the holder.

FIGS. 3A and 3B shows a preferable cell 26 and a cellholder 30 used in a sample part 2 in FIG. 2. The cell 26 is a spherical quartz flow cell provided with cylindrical inlet 26a and outlet 26b of sample gas. The cell holder 30 consists of two members 30a and 30b which are superposed with each other, and is provided with two cylindrical cell holding parts 32a and 32b, an integrating sphere part 34 linked with the cell holding parts 32a and 32b, an inlet hole 36 for irradiating the cell 26 which is held by the cell-holder 30 with excitation light through the integrating sphere part 34 and an outlet hole 38 opening outwardly for taking out scattered light generated from a sample in the cell 26 to the exterior through the integrating sphere part 34.

The excitation light come in the integrating sphere part 34 reflects repeatedly resulting in reinforcement of the scattered light.

The half mirrors 9 and 16 may be transparent flat glasses laid obliquely on an optical path. A transparent flat glass is favorable to increasing a transmitted light intensity. The mirror 18 may also be a transparent flat glass.

Examples of some expiration components measured by the aforementioned measuring apparatus shown in FIGS. 2 and 3 are now described.

Figure 4:
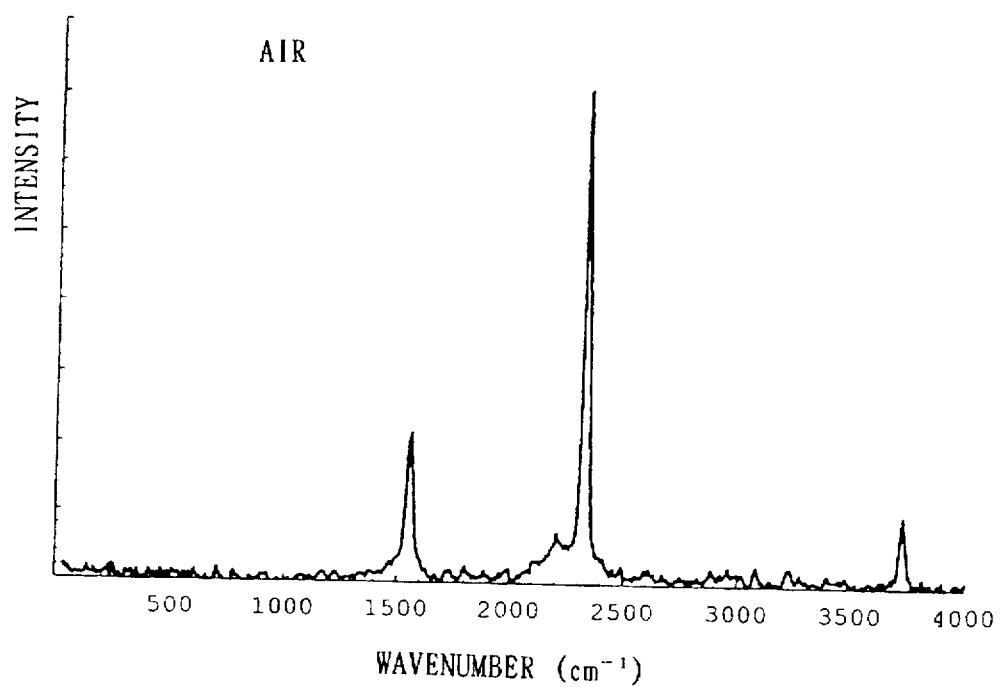
FIG. 4 illustrates the spectra of oxygen, nitrogen and water vapor.

FIG. 4 illustrates the spectra of oxygen, nitrogen and water (water vapor) contained in the air. The peaks around 1561 $cm^{-1}$, around 2334 $cm^{-1}$ and around 3659 $cm^{-1}$ are derived from oxygen gas, nitrogen gas and water vapor respectively.

Figure 5:
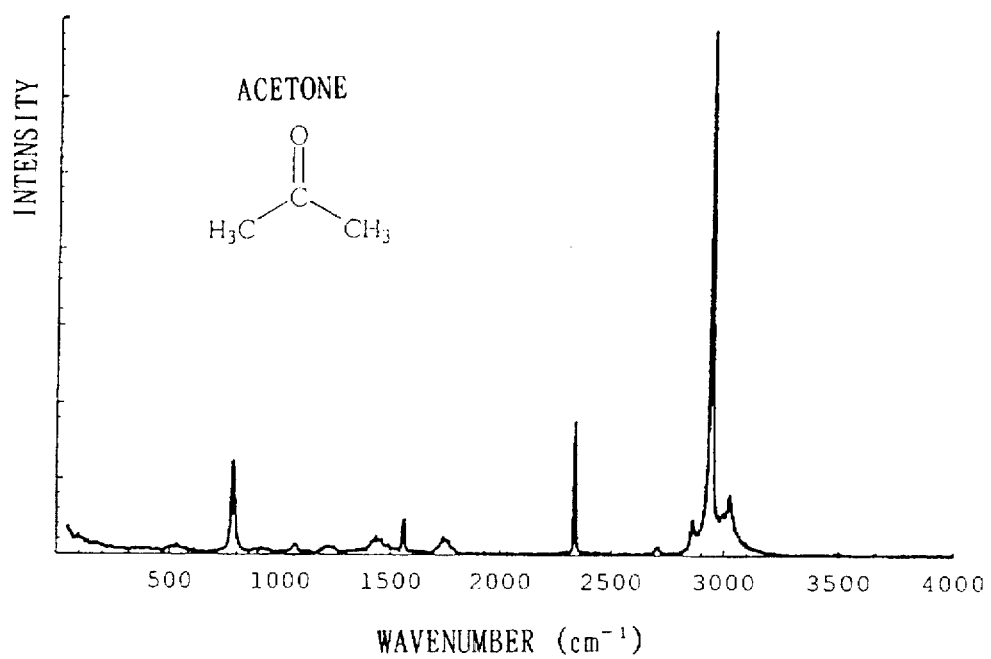
FIG. 5 illustrates the spectrum of acetone gas.

FIG. 5 illustrates the spectrum of acetone gas.

Figure 6:
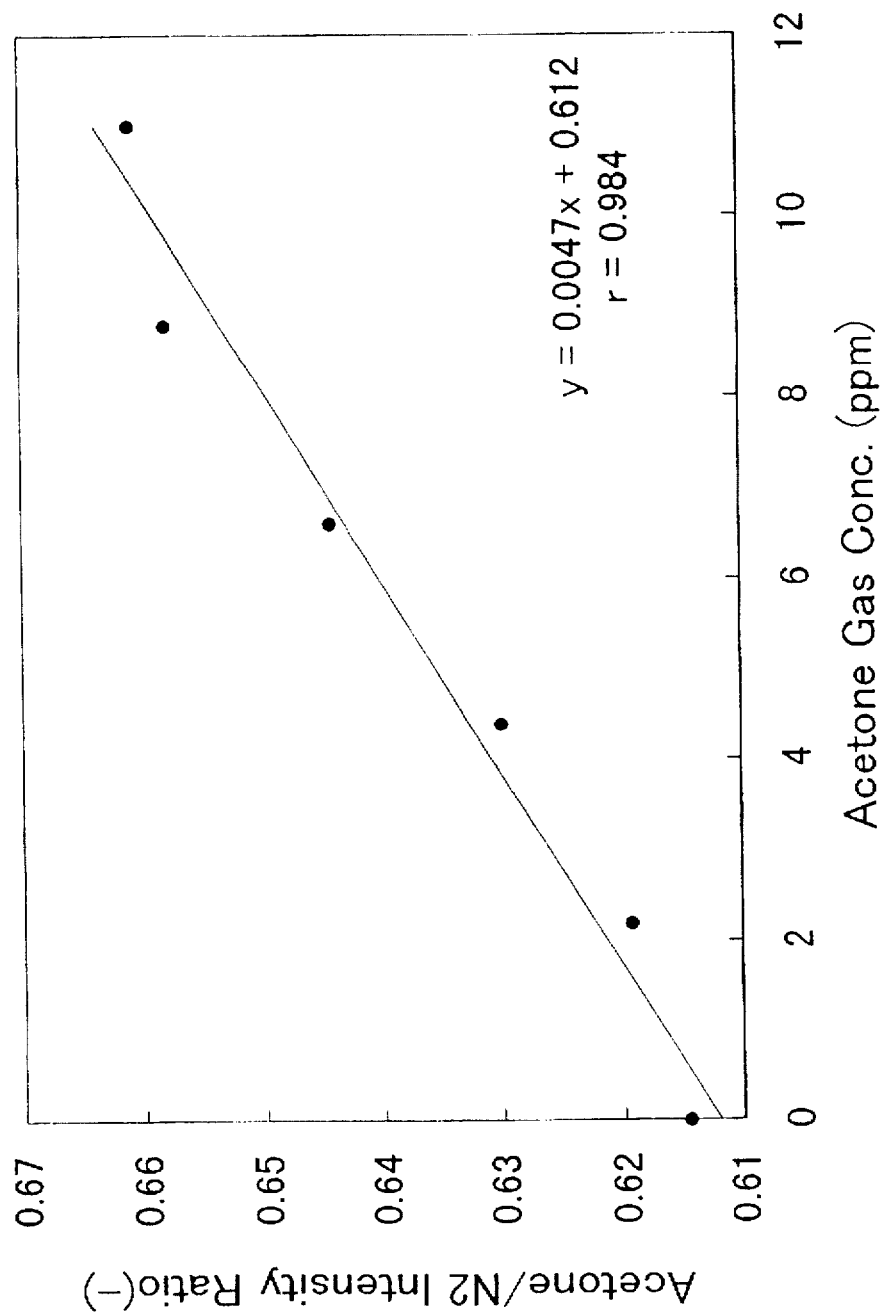
FIG. 6 illustrates the correlation between peak intensity of acetone gas around 2940 $cm^{-1}$ and the concentration.
Figure 7:
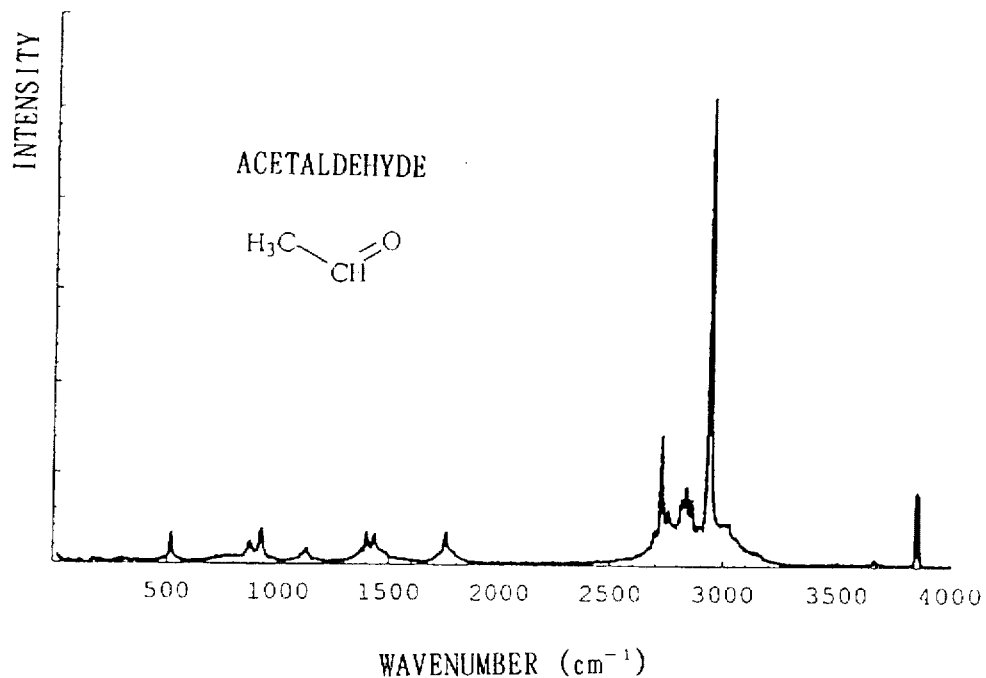
FIG. 7 illustrates the Raman spectrum of acetaldehyde gas.
Figure 8:
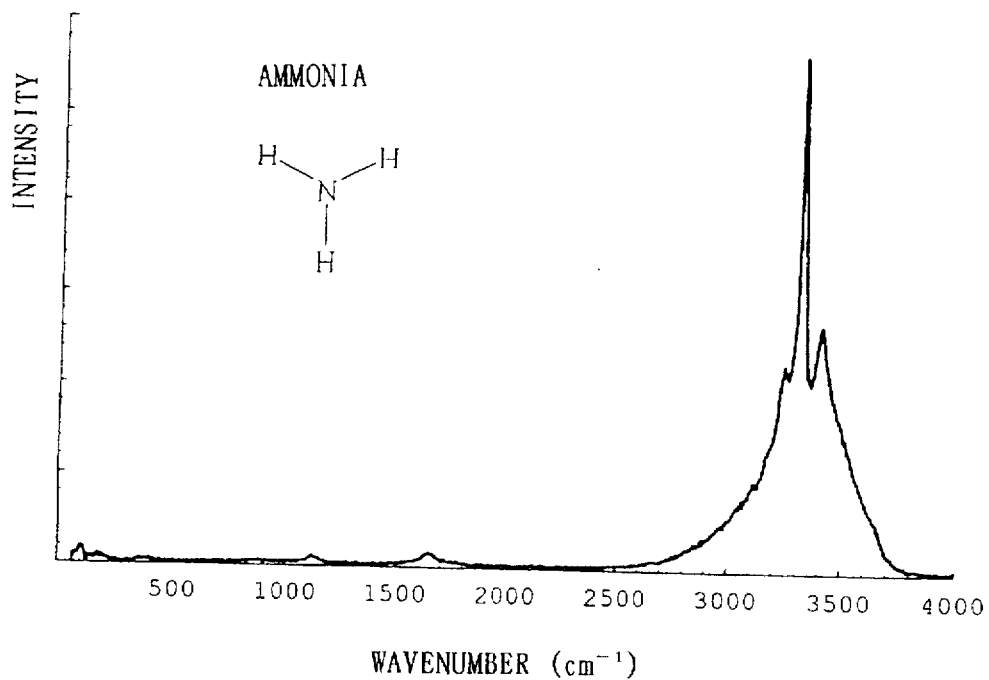
FIG. 8 illustrates the Raman spectrum of ammonia gas.
Figure 9:
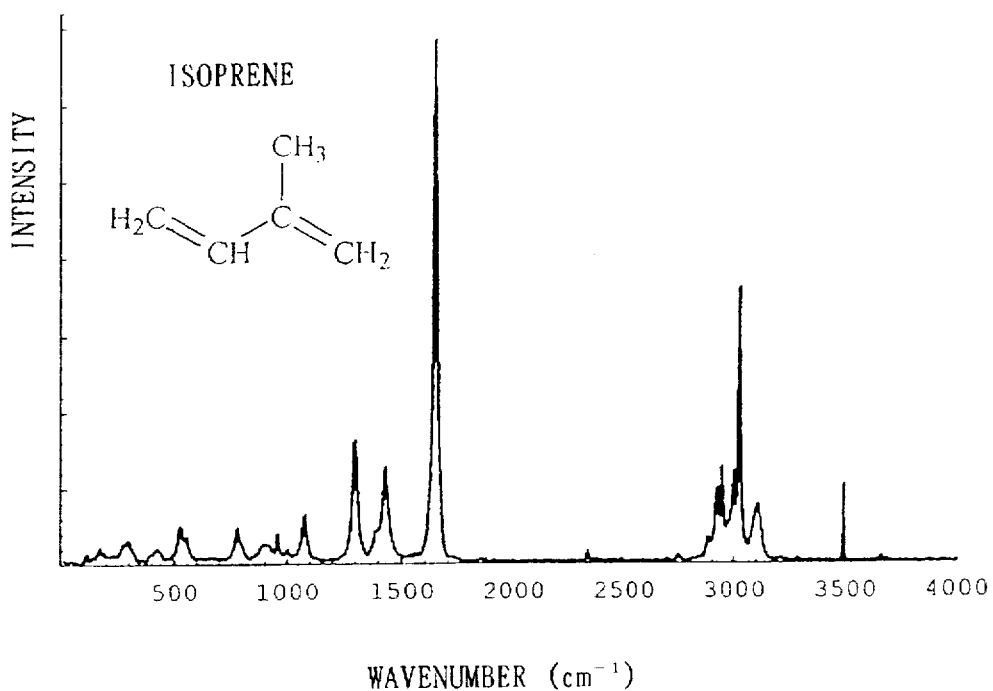
FIG. 9 illustrates the Raman spectrum of isoprene gas.
Figure 10:
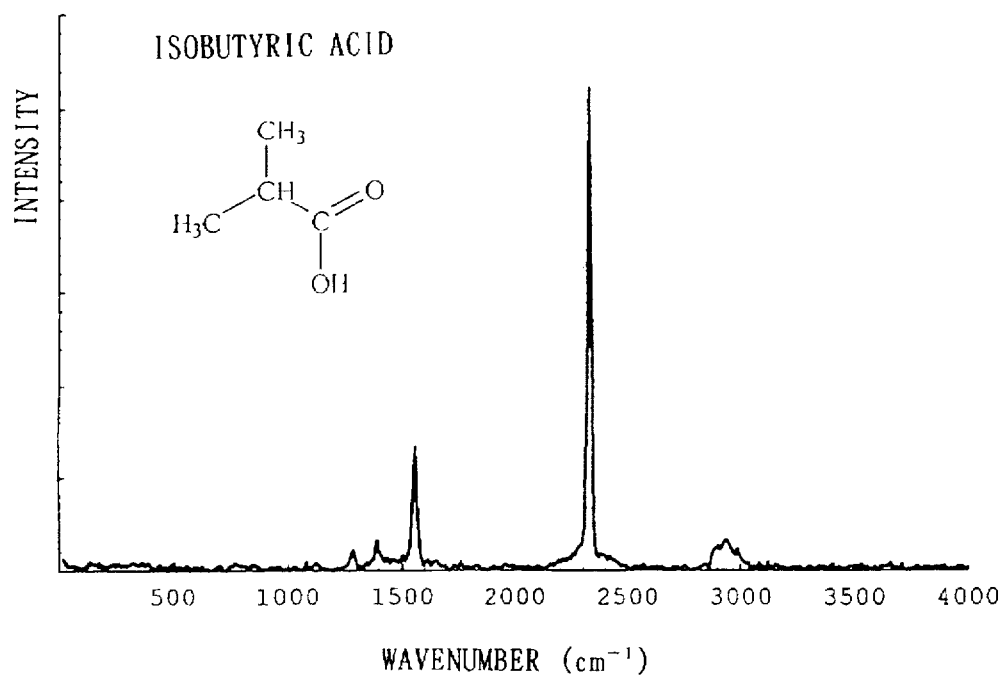
FIG. 10 illustrates the Raman spectrum of isobutyric acid gas.
Figure 11:
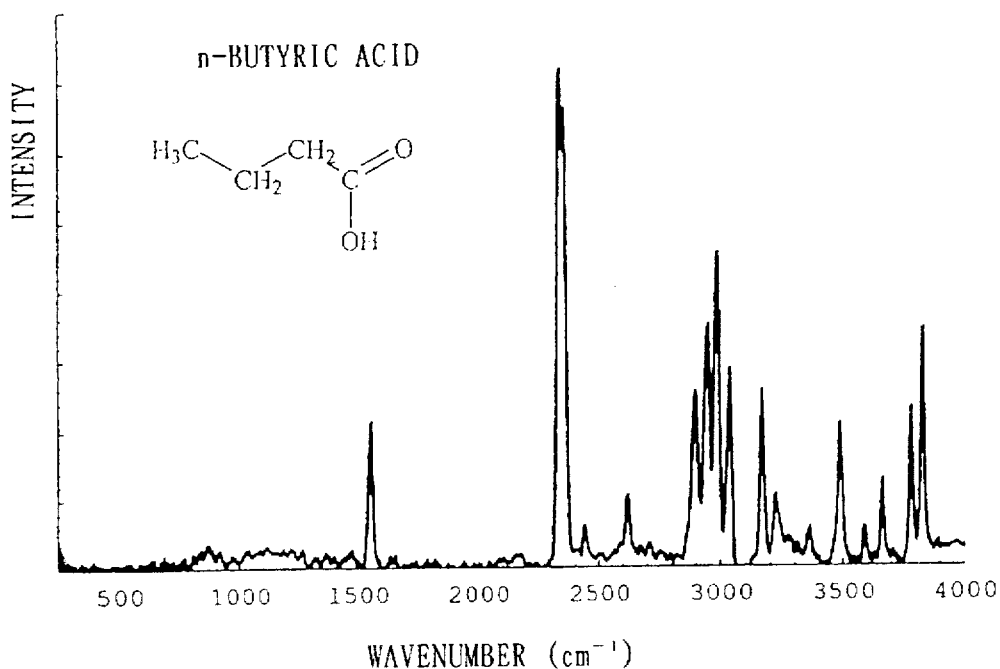
FIG. 11 illustrates the Raman spectrum of n-butyric acid gas.
Figure 12:
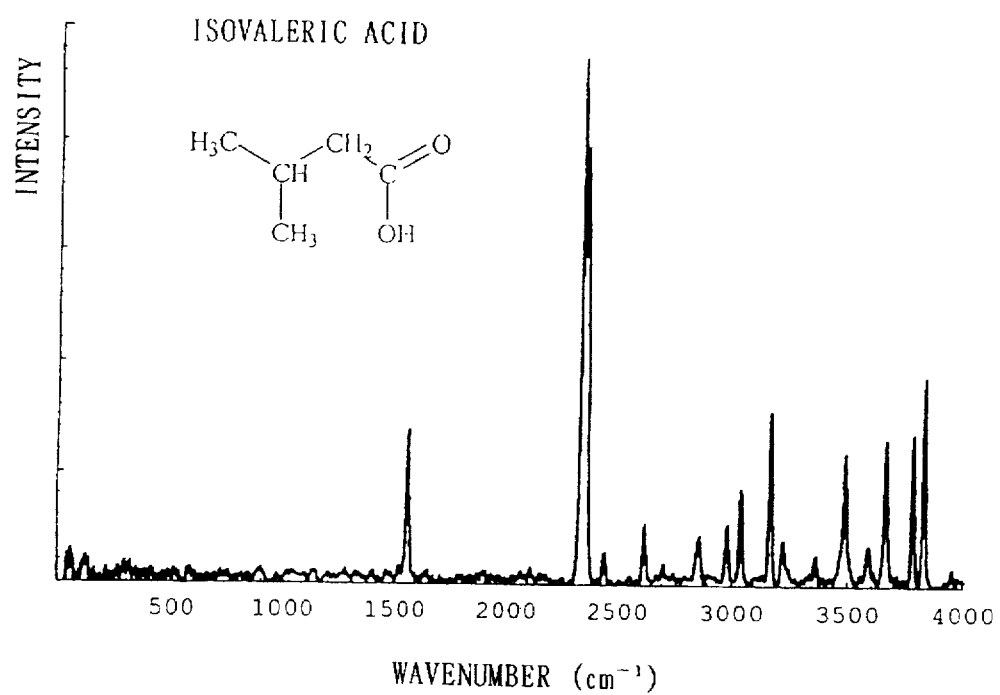
FIG. 12 illustrates the Raman spectrum of isovaleric acid gas.
Figure 13:
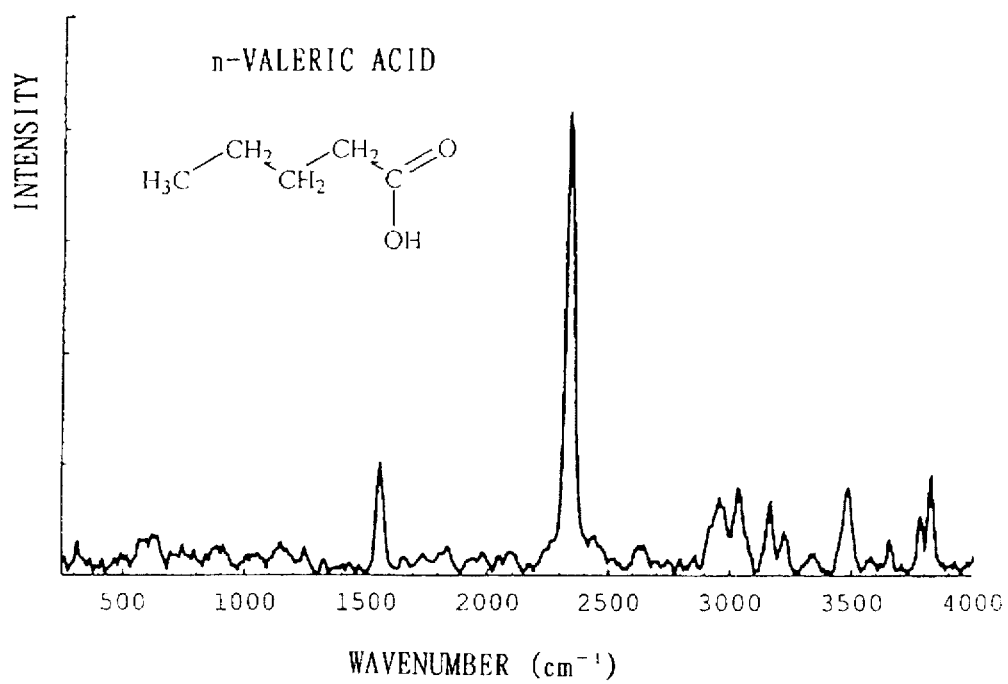
FIG. 13 illustrates the Raman spectrum of n-valeric acid gas.
Figure 14:
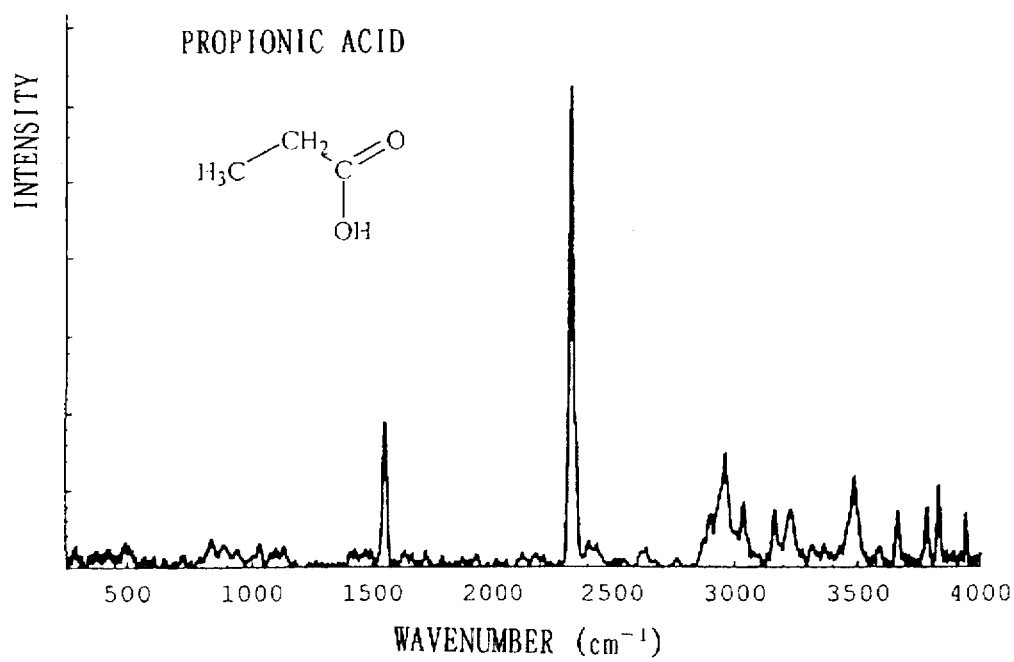
FIG. 14 illustrates the Raman spectrum of propionic acid gas.
Figure 15:
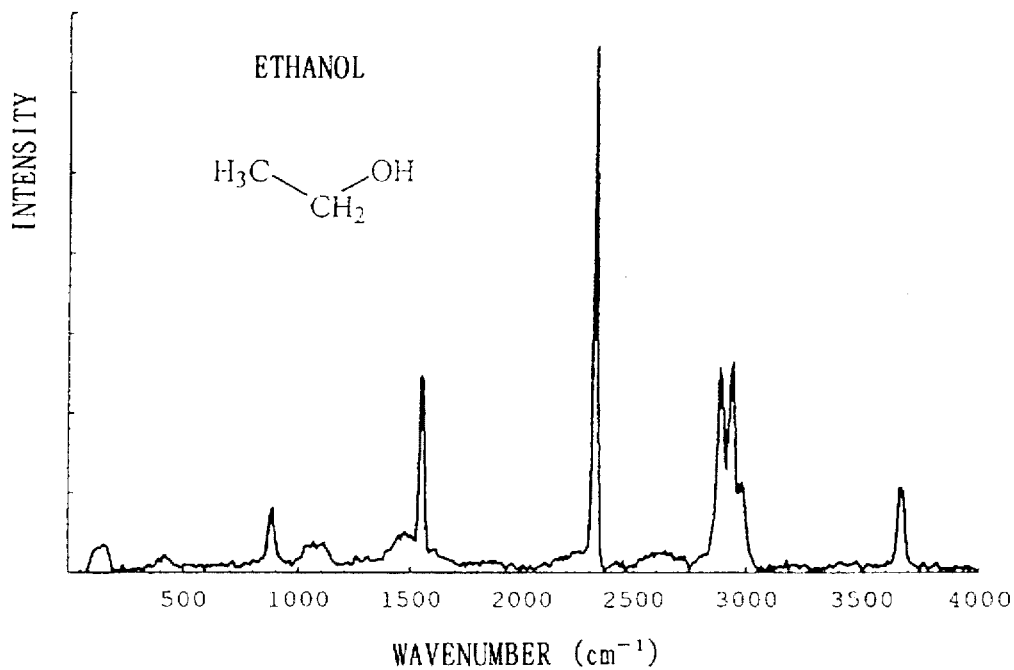
FIG. 15 illustrates the Raman spectrum of ethanol gas.
Figure 16:
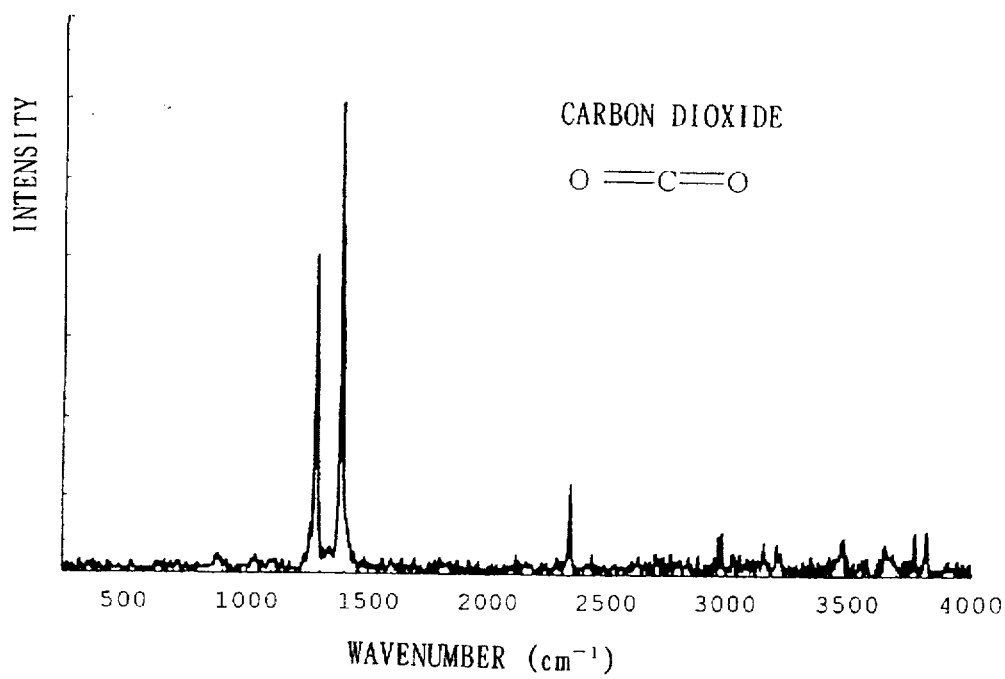
FIG. 16 illustrates the Raman spectrum of carbon dioxide gas.
Figure 17:
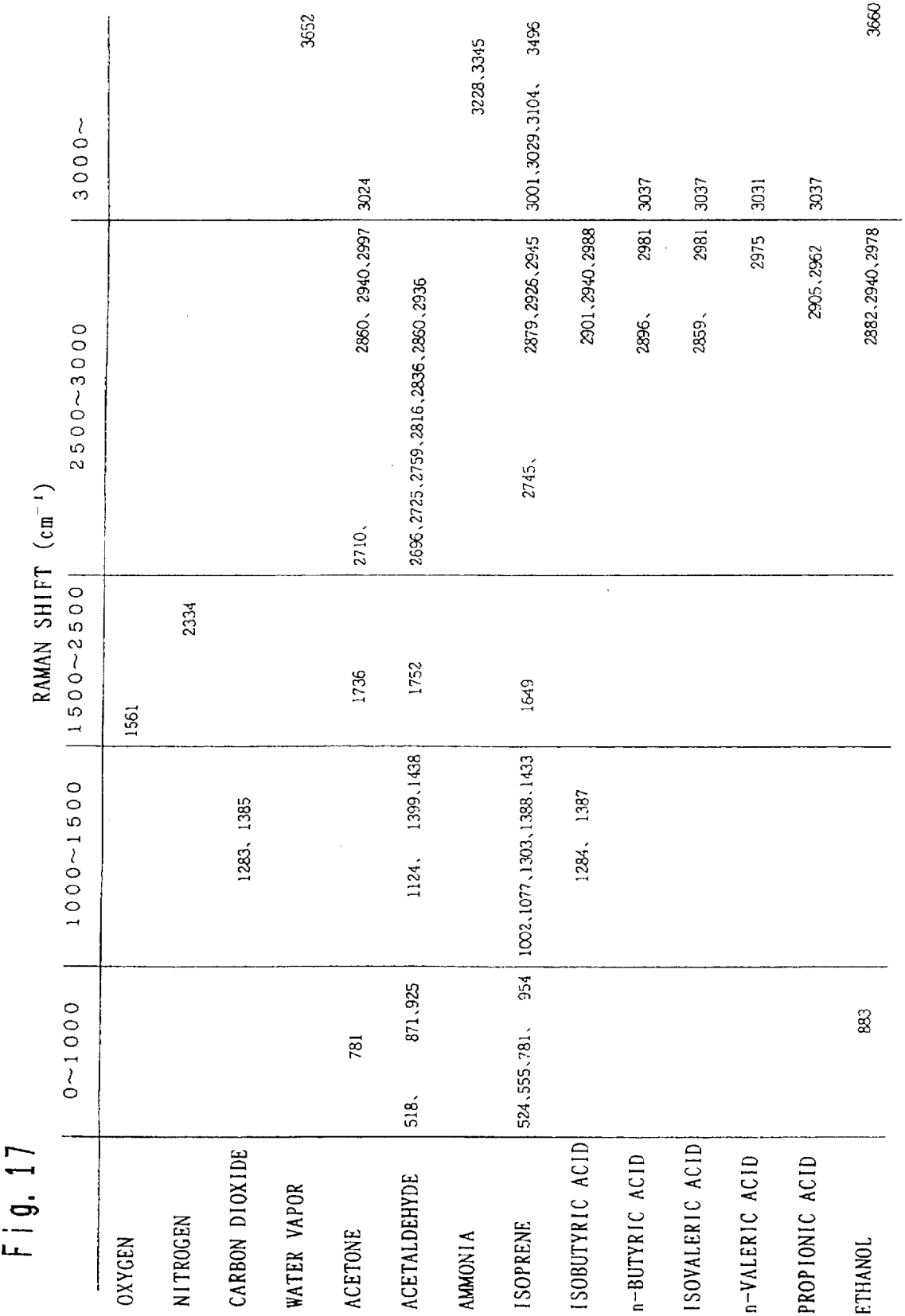
FIG. 17 illustrates peak positions of expiration substances suitable for quantitative measurement.

FIG. 6 illustrates a result of the correlation between peak strength around 2940 $cm^{-1}$ in the spectrum of FIG. 5 and the concentration. The peak strength in FIG. 6 is corrected by $N_2$ intensity. The correlation coefficient R is 0.984. From this result, it is understood that a linear relation is obtained between the peak intensity and the concentration even in low concentration gas such as an expiration component. It is understood that, when such correlation between the peak intensity (or a peak area) and the concentration is previously measured as to each component, each component can be determined by utilizing the same as a calibration curve.

FIGS. 7 to 16 show Raman spectra of acetaldehyde gas, ammonia gas, isoprene gas, isobutyric acid gas, n-butyric acid gas, isovaleric acid gas, n-valeric acid gas, propionic acid gas, ethanol gas and carbon dioxide gas respectively.

Although the present invention has been described and illustrated in detail, it is clearly understood that the same is by way of illustration and example only and is not to be taken by way of limitation, the spirit and scope of the present invention being limited only by the terms of the appended claims.

We claim:

1. An optical measuring method for expiration components, comprising the steps of:
   previously selecting wavelengths having excellent correlations between component concentrations as well as nitrogen concentration and Raman spectral intensity values as measuring wavelengths being specific to said components as well as nitrogen as to respective said components to be measured as well as nitrogen;
   previously preparing a calibration curve as to Raman spectral intensity ratios of respective said components to nitrogen and concentrations as to respective said expiration components:
   irradiating an expiration specimen with Raman excitation light;
   measuring Raman spectra at said measuring wavelengths being previously selected as to said components to be measured as well as nitrogen for obtaining said Raman spectral intensity ratios of said components to said Raman spectral of intensity of nitrogen; and
   quantitatively analyzing said components on the basis of Raman spectral intensity values of said components.

2. The optical measuring method for expiration components in accordance with claim 1, wherein
   said wavelengths having excellent correlations between concentrations and Raman spectral intensity values of said components are wavelengths having correlation coefficients R of at least 0.8.

3. The optical measuring method for expiration components in accordance with claim 2, wherein
   components in a group consisting of oxygen, nitrogen, carbon dioxide, water vapor, acetone, acetaldehyde, ammonia, isoprene, isobutyric acid, n-butyric acid, isovaleric acid, n-valeric acid, propionic acid and ethanol are contained as said expiration components to be measured, and said measuring wavelengths for said components being selected:

from around 1530 to 1590 $cm^{-1}$ in wavenumber for oxygen, from around 2304 to 2364 $cm^{-1}$ in wavenumber for nitrogen, from around 1255 to 1315 $cm^{-1}$ or around 1335 to 1415 $cm^{-1}$ in wavenumber for carbon dioxide, from around 751 to 811 $cm^{-1}$, around 1706 to 1766 $cm^{-1}$, around 2680 to 2740 $cm^{-1}$, around 2830 to 2967 $cm^{-1}$ or around 2967 to 3054 $cm^{-1}$ in wavenumber for acetone, from around 488 to 518 $cm^{-1}$, around 841 to 901 $cm^{-1}$, around 895 to 955 $cm^{-1}$, around 1084 to 1144 $cm^{-1}$, around 1369 to 1468 $cm^{-1}$, around 1722 to 1782 $cm^{-1}$, around 2666 to 2786 $cm^{-1}$, around 2786 to 2890 $cm^{-1}$ or around 2906 to 2966 $cm^{-1}$ in wavenumber for acetaldehyde, from around 494 to 585 $cm^{-1}$, around 751 to 811 $cm^{-1}$, around 924 to 1042 $cm^{-1}$, around 1047 to 1107 $cm^{-1}$, around 1273 to 1343 $cm^{-1}$, around 1358 to 1463 $cm^{-1}$, around 1619 to 1679 $cm^{-1}$, around 2715 to 2775 $cm^{-1}$, around 2849 to 2909 $cm^{-1}$, around 2896 to 2975 $cm^{-1}$, around 2975 to 3059 $cm^{-1}$, around 3074 to 3144 $cm^{-1}$ or around 3466 to 3526 $cm^{-1}$ in wavenumber for isoprene, from around 3198 to 3258 $cm^{-1}$ or around 3315 to 3375 $cm^{-1}$ in wavenumber for ammonia, from around 1254 to 1314 $cm^{-1}$, around 1357 to 1417 $cm^{-1}$ or around 2871 to 3018 $cm^{-1}$ in wavenumber for isobutyric acid, from around 2866 to 2926 $cm^{-1}$, around 2951 to 3011 $cm^{-1}$ or around 3011 to 3067 $cm^{-1}$ in wavenumber for n-butyric acid, from around 2829 to 2889 $cm^{-1}$, around 2951 to 3011 $cm^{-1}$ or around 3011 to 3067 $cm^{-1}$ in wavenumber for isovaleric acid, from around 2945 to 3005 $cm^{-1}$ or around 3005 to 3061 $cm^{-1}$ in wavenumber for n-valeric acid, from around 2875 to 2935 $cm^{-1}$ or around 2935 to 2962 $cm^{-1}$ in wavenumber for propionic acid, and from around 853 to 913 $cm^{-1}$, around 2852 to 2910 $cm^{-1}$, around 2910 to 3008 $cm^{-1}$ or around 3630 to 3690 $cm^{-1}$ in wavenumber for ethanol.

4. The optical measuring method for expiration components in accordance with claim 1, wherein after said expiration specimen in a cell is irradiated with Raman excitation light, scattered light from said expiration specimen is separated into its spectral components, and wavelength regions to be measured are simultaneously detected through a multi-channel detector.

5. The optical measuring method for expiration components in accordance with claim 1, wherein an excitation light component is also detected at the same time along with Raman scattered light by said multi-channel detector, for correcting Raman scattered light intensity on the basis of detected intensity of said excitation light component.

6. The optical measuring method for expiration components in accordance with claim 1, wherein said step of irradiating said expiration specimen further includes the steps of dividing an excitation light beam from a light source part into 1) a sample beam which irradiates said expiration specimen and 2) a correction beam which corrects fluctuation of spectral light intensity caused by fluctuation of excitation light intensity and said step of measuring Raman spectra includes a step of recombining scattered light from said sample beam after irradiating said expiration specimen and said correction beam.

7. The optical measuring method for expiration components in accordance with claim 1, wherein said wavelengths having excellent correlations between concentrations and Raman spectral intensity values of said components are wavelengths having correlation coefficients R of at least 0.9.

8. The optical measuring method for expiration components in accordance with claim 7, wherein components in a group consisting of oxygen, nitrogen, carbon dioxide, water vapor, acetone, acetaldehyde, ammonia, isoprene, isobutyric acid, n-butyric acid, isovaleric acid, n-valeric acid, propionic acid and ethanol are contained as said expiration components to be measured, and said measuring wavelengths for said components being selected:

from around 1530 to 1590 $cm^{-1}$ in wavenumber for oxygen, from around 2304 to 2364 $cm^{-1}$ in wavenumber for nitrogen, from around 1255 to 1315 $cm^{-1}$ or around 1335 to 1415 $cm^{-1}$ in wavenumber for carbon dioxide, from around 751 to 811 $cm^{-1}$, around 1706 to 1766 $cm^{1}$, around 2680 to 2740 $cm^{-1}$, around 2830 to 2967 $cm^{-1}$ or around 2967 to 3054 $cm^{-1}$ in wavenumber for acetone, from around 488 to 518 $cm^{-1}$, around 841 to 901 $cm^{-1}$, around 895 to 955 $cm^{-1}$, around 1084 to 1144 $cm^{-1}$, around 1369 to 1468 $cm^{-1}$, around 1722 to 1782 $cm^{-1}$, around 2666 to 2786 $cm^{-1}$, around 2786 to 2890 $cm^{-1}$ or around 2906 to 2966 $cm^{-1}$ in wavenumber for acetaldehyde, from around 494 to 585 $cm^{-1}$, around 751 to 811 $cm^{-1}$, around 924 to 1042 $cm^{-1}$, around 1047 to 1107 $cm^{-1}$, around 1273 to 1343 $cm^{-1}$, around 1358 to 1463 $cm^{-1}$, around 1619 to 1679 $cm^{-1}$, around 2715 to 2775 $cm^{-1}$, around 2849 to 2909 $cm^{-1}$, around 2896 to 2975 $cm^{-1}$, around 2975 to 3059 $cm^{-1}$, around 3074 to 3144 $cm^{-1}$ or around 3466 to 3526 $cm^{-1}$ in wavenumber for isoprene, from around 3198 to 3258 $cm^{-1}$ or around 3315 to 3375 $cm^{-1}$ in wavenumber for ammonia, from around 1254 to 1314 $cm^{-1}$, around 1357 to 1417 $cm^{-1}$ or around 2871 to 3018 $cm^{-1}$ in wavenumber for isobutyric acid, from around 2866 to 2926 $cm^{-1}$, around 2951 to 3011 $cm^{-1}$ or around 3011 to 3067 $cm^{-1}$ in wavenumber for n-butyric acid, from around 2829 to 2889 $cm^{-1}$, around 2951 to 3011 $cm^{-1}$ or around 3011 to 3067 $cm^{-1}$ in wavenumber for isovaleric acid, from around 2945 to 3005 $cm^{-1}$ or around 3005 to 3061 $cm^{-1}$ in wavenumber for n-valeric acid, from around 2875 to 2935 $cm^{-1}$ or around 2935 to 2962 $cm^{-1}$ in wavenumber for propionic acid, and from around 853 to 913 $cm^{-1}$, around 2852 to 2910 $cm^{-1}$, around 2910 to 3008 $cm^{-1}$ or around 3630 to 3690 $cm^{-1}$ in wavenumber for ethanol.

* * * * *